United States Patent [19]

Ledergerber

[11] Patent Number: 5,779,734
[45] Date of Patent: Jul. 14, 1998

[54] COVERING FOR AN IMPLANTABLE PROSTHETIC DEVICE

[76] Inventor: Walter J. Ledergerber, 29502 Anna Maria, Laguna Niguel, Calif. 92677

[21] Appl. No.: 821,225

[22] Filed: Mar. 20, 1997

Related U.S. Application Data

[63] Continuation of Ser. No. 198,651, Feb. 18, 1994, Pat. No. 5,653,755, which is a continuation of Ser. No. 837,284, Feb. 18, 1992, abandoned, which is a continuation of Ser. No. 137,871, Dec. 22, 1987, Pat. No. 5,282,856.

[51] Int. Cl.$^6$ ............... A61F 2/12; A61F 2/02
[52] U.S. Cl. .................................. 623/8; 623/11
[58] Field of Search ................... 623/7, 8, 11, 1, 623/66

[56] References Cited

U.S. PATENT DOCUMENTS

| | | | |
|---|---|---|---|
| 4,428,082 | 1/1984 | Naficy | 623/8 |
| 4,605,412 | 8/1986 | La Forest et al. | 623/8 |
| 4,615,704 | 10/1986 | Frisch | 623/8 |
| 4,643,733 | 2/1987 | Beeker | 623/11 |
| 4,650,487 | 3/1987 | Chaglassian | 623/8 |

*Primary Examiner*—Debra S. Brittingham
*Attorney, Agent, or Firm*—Lyon & Lyon LLP

[57] ABSTRACT

An implant and coverings for an implant for use in the human body are disclosed. Coverings for implants are constructed to present a biocompatible surface to the body and to provide a textured surface which serves to disorganize scar tissue which forms around the implant. Filaments of expanded PTFEe are attached to a stretch fabric backing in a loose weave configuration. Silicone molded in geometric patterns may be employed to present a textured surface. Compressive structures may be beneficially used on the surface of the implant or in the interior of the implant. Foam is one such compressive structure. Hexagonally shaped compressive cells containing fluid, gas, gel or foam are adapted to receive an insert which contains an outer biocompatible coating. A valve or port is provided to communicate between the cell and the body. Expansion means may be provided to expand the implant in a desired direction.

1 Claim, 11 Drawing Sheets

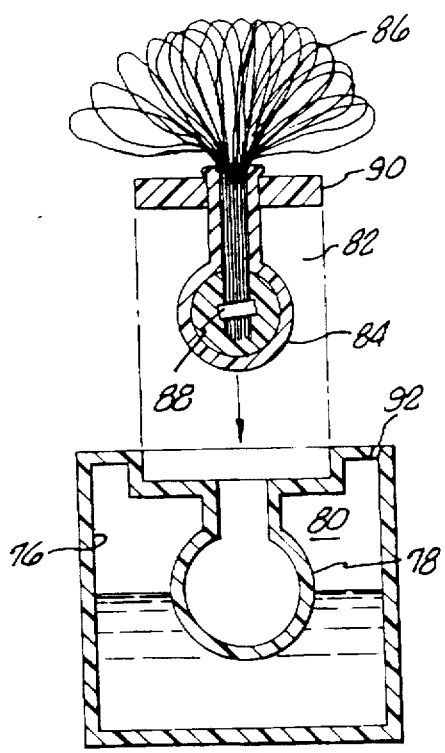
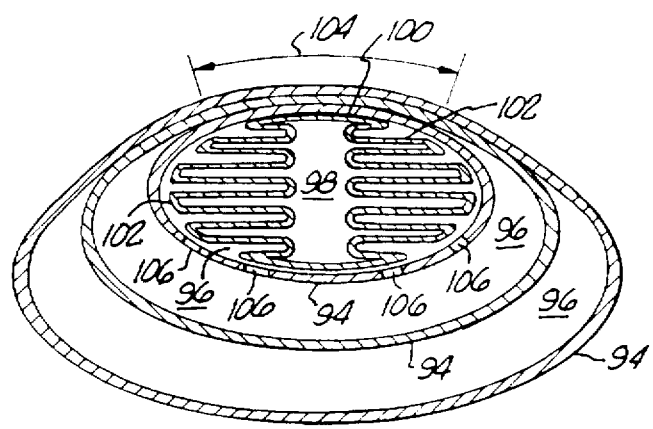
*fig.17.*
*fig.18.*
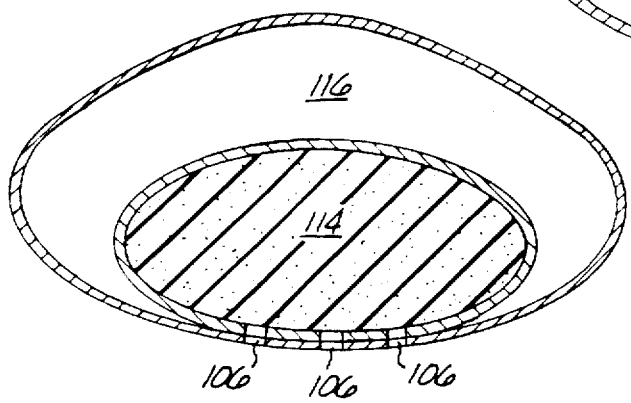
*fig.19.*

COVERING FOR AN IMPLANTABLE PROSTHETIC DEVICE

This is a continuation of application Ser. No. 08/198,651, filed Feb. 18, 1994, now U.S. Pat. No. 5,653,755 which is a continuation of Ser. No. 07/837,284, filed Feb. 18, 1992, now abandoned, which is a continuation of Ser. No. 07/137,871, filed Dec. 22, 1987, now issued as U.S. Pat. No. 5,282,856.

FIELD OF THE INVENTION

This invention relates to implantable prosthetic devices and especially to prosthetic devices for reconstruction or augmentation of the female breast.

BACKGROUND OF THE INVENTION

Implantable prosthetic devices have been used in numerous locations in the body. The most common use has been for restoring or improving upon normal body contour or augmenting as well as reconstructing the female breast. The most common breast prosthesis is similar to that disclosed in U.S. Pat. No. 3,293,663 to Cronin, in which there is a flexible elastomeric container, typically silicone, which is filled with a soft gel, typically silicone gel or a saline solution or a combination of both.

It is known that when a prosthetic device, including the Cronin type device, is implanted in the body, fibrous scar tissue encapsulates the device. This encapsulation leads to a problem of spherical scar contracture. As the scar tissue surrounds the prosthetic device it tends to contract, thereby causing the gel filled sac to assume a minimum surface area configuration or spherical configuration. The problem of spherical scar contracture causes the breast implant to change from a shape approximating that of a natural human breast to that of a tennis ball.

Numerous solutions to the spherical scar contracture problem have been proposed. Friesch U.S. Pat. No. 4,205,401 proposes the use of a relatively rigid restraining means which is contained within the fluid filled sac to thereby reduce the tendency of the tissue to distort the prosthesis into a sphere. Hamas U.S. Pat. No. 4,264,990 discloses the use of a prosthesis which contains a flexible backing material containing at least one internal passageway or compartment into which a rigidifying material may be forced or emplaced. In this way the backing becomes inflexible in an attempt to prevent spherical encapsulation of the implant. Hamas U.S. Pat. No. 4,531,244 discloses a prosthesis containing an outer envelope composed of a plurality of firm protruberances distributed substantially equally thereover. As scar contracture occurs, the relatively rigid protruberances are forced toward the gel filled sac, press on the gel filled sac, the gel flowing under pressure into the space between the protruberances.

The amount of spherical scar contracture which develops varies from patient to patient, and sometimes even differently respecting two implants in a single patient. The length of time which spherical scar contracture takes to develop also varies from patient to patient. Knowledge as to the etiologic factors behind spherical scar contracture is still developing. Some contributing factors are believed to be the tendency of the human body to wall off foreign substances, the formation of blood clot, infection, the presence of small operating field contaminants such as talcum powder, silicone gel bleed through elastomer membrane and chronic irritation due to movement of the implant at the interface between the body tissues and implanted materials.

Other problems with breast implants include postimplantation asymmetry, breast ptosis and implant rupture. These problems, along with spherical scar contracture, can lead to patient discomfort, unacceptable deformation and shape of the breast and implant, loss of breast volume, gel dissemination and migration to distant points within the body, bleeding after surgical lysis of spherical contractures and even life-threatening systemic infection. In severe cases it is necessary to reoperate to remove or replace the prosthesis and to incise or excise the scar capsule or to remove blood clots which may result from closed lysis ("closed capsulotomy") of the contractures. The risks of reoperating include the risks of anesthesia, infection, additional scarring, other morbidity, and economic costs. When the results of the reconstructive or augmentative implantation are less than anticipated a loss of self esteem in the patient results.

Brauman U.S. Pat. No. 4,648,880 discloses the use of a flexible container with a soft gel or fluid filling and an outer plastic or polymeric covering bonded to the flexible container and substantially encompassing the container. The outer covering is preferably made from Dacron or Teflon and has numerous pores or interstices as well as a rough textured external surface. The covering is believed to disperse or disorganize the forces of encapsulating scar tissue sufficient to avoid formation of a spherical capsular contracture. Brauman finds that the use of knitted polyester fiber such as Dacron, is found to be superior because it provides more elasticity and tissue ingrowth.

While it is believed that dispersion or disorganization of the scar tissue is beneficial in reducing spherical capsular contraction, it has proved extremely difficult to construct useful coverings out of Teflon. While Teflon is an exceptionally good biocompatible material, it has proved difficult to utilize as a covering material due to the difficulty of attachment to an enclosed elastomeric sac.

Other attempts have been made to limit spherical scar contracture, implant/breast deformation, or to deal with it once it has occurred. Approaches utilized previously include: (1) a normal saline barrier contained within its own silicone elastomer shell placed between the elastomer-encased gel portion of the implant and the body tissue, (2) overfilling the prosthesis at the time of implantation and subsequently bleeding off excess fluid to allow for a softer implant, (3) underfilling the implant at the time of implantation and subsequently adding fluid to counteract the forces of scar contracture with perhaps later bleed off, (4) using steroids, either injected into the tissue surrounding the implant or into the interior of the implant or administered perorally in the post-operative period, (5) closed lysis of the contracture by applying pressure external to the breast sufficient to tear the scar capsule, (6) open lysis of the scar contracture through a second larger incision and more aggressive and extensive surgery to remove or weaken the scar capsule, (7) removal of the submammary implant and placing a different implant either into the submammary plane or submuscularly, (8) massage of the breast and applying external pressure in order to keep the capsule soft and pliable, and (9) massage of the breast in a circular fashion to maintain an oversized "pocket" significantly larger than the implant.

SUMMARY OF THE INVENTION

The present invention is directed to: (A) the use of a covering for a prosthesis which has high tissue ingrowth, biocompatibility, low reactivity and scar tissue formation and which disorganizes scar tissue that does form, thereby decreasing its ability to contract. Expanded PTFE (PTFEe) is used in the preferred embodiment of this invention. The PTFEe is configured for and may be attached to the elastomeric material such that the breast prosthesis is able to maintain a soft and natural suppleness, or it may remain entirely unattached as an enveloping sheetlike element. In one embodiment, a complex woven PTFEe filament or ribbon is sewn or affixed to a backing material, such as a Dacron or Nylon stretch weave embedded in silicone elastomer membrane. A drawstring closure or other device may be used to enclose the implant in the covering. Numerous coverings are possible in which a tube of PTFEe is modified by cutting to provide a suitable covering. One such example consists of cutting a tube in an annular configuration with a plurality of extending fingers. Multiple such elements may be affixed to the Dacron or Nylon stretch weave material cited above.

The present invention also is directed to: (B) the use of compressive structures which may be external and/or internal. Coverings may be provided which are relatively compressible in response to capsular contraction. In one embodiment the covering consists of a plurality of hexagonally shaped cells which contain a biocompatible fluid which may be expelled from the cells under the pressure of capsular contraction. Compressive structures may also be provided within the implant itself. For example, gas or biocompatible fluid-filled elements or chambers within the implant may be compressed under the action of the contractile forces. Another embodiment utilizes biocompatible fluid filled foam elements as partially compressible structures either inside or outside the implant.

The present invention is further directed to: (C) providing variations in the compressibility and stability of the implant by utilizing a plurality of evaginations in the implant itself or by utilizing toroid structures which are affixed together or by enclosing deformable or mobile silicone elastomer structures within a containment including a fluid or gel matrix.

The present invention is further directed to: (D) providing for projection of a portion of the implant. Projection of the apex of the implant, for example, can be enhanced by filling special elements with fluid before, during or after surgical implantation.

Therefore, it is an object of this invention to: (1) provide an implantable prosthesis which resists the formation of spherical scar contracture, to (2) decrease the amount of scar tissue that forms at the implant/body interface, to (3) disperse and to disorganize the forces of scar contracture within the scar capsule that actually forms, to (4) accommodate to the net force of scar contracture that does occur, to (5) permit easy introduction and removal of the implant if removal should become necessary.

It is a further object of this invention to provide an implantable prosthesis which permits (6) postimplantation accommodation of total volume, either more or less than the volume at implantation.

It is a further object of this invention to provide an implantable mammary prosthesis which permits (7) postimplantation accommodation of implant projection which is defined as the distance from the chest wall pole of the implant to the opposite pole of the implant.

It is a further object of this invention to provide an implantable prosthesis which (8) prevents or greatly reduces gel bleed by virtue of inhibition of migration of gel through both the outermost elastomer membrane and PTFEe and other coverings.

It is a further object of this invention to provide for (9) a decreased rate of wound infections.

It is a further object of this invention to (10) greatly decrease the rate of reoperations for a variety of problems associated with breast prostheses by virtue of enhanced performance due to improved design.

BRIEF DESCRIPTION OF THE DRAWINGS

The above objects and advantages of this invention will be more easily understood with reference to the following drawings and detailed description. In the drawings:

FIG. 17 shows a detailed cross-section of a cell from which biocompatible fluid may be expelled under the contractile force of the scar tissue capsule as well as a scheme for a "floating" fixation of solid PTFE discs or other suitable material or PTFEe filament or ribbon in special attachment receptacles.

FIG. 18 shows a preferred embodiment of a pressure accommodation element consisting of a gas-filled element with a plurality of hyperevaginations in disc-like configuration. This element is contained within a perforated elastomer shell which serves to fixate and to locate the element in apposition to a desired location on the wall of an internal fluid compartment of the implant. This element when configured in the embodiment illustrated also serves to provide for projection of the apex of the implant when certain wall thicknesses and appropriately stretchable silicone elastomer is utilized.

FIG. 19 shows a pressure accommodation element consisting of a polyurethane or other biocompatible foam contained substantially within an enveloping chamber of silicone gel or normal saline or other biocompatible fluid or other structural element. The pressure accommodation element is affixed to the wall of the outer chamber. The wall is perforated or has other means for allowing transfer of biocompatible fluids in and out of the foam-filled element. These elements may be single or multiple in a given implant design.

FIG. 26 shows detail of the expansion chamber and solid toroid structures as well as the PTFEe sheets which are interposed between.

DETAILED DESCRIPTION OF THE PREFERRED EMBODIMENTS

The implant coverings usable in connection with this invention may be manufactured from any material which promotes limited tissue ingrowth into the material, and has a high biocompatibility and low reactivity and disorganizes scar tissue at the implant/ body interface. Expanded PTFE (PTFEe) is a preferred material for this invention. PTFEe is sold under the tradename Gortex and is readily available. The expanded ultrastructure of this material is associated with a high degree of ultramicroporosity which invites tissue ingrowth. The material is approximately 50% air by volume. It is extremely strong yet soft, smooth, pliable, compressible and stretchable. Gortex is readily available in sheet form of various thicknesses, as round filaments of various diameters, and as tubes of various diameters and wall thicknesses. PTFEe sheeting stretches to a limited extent along a given axis, however resists stretching along all axes simultaneously. It is extremely biocompatible having been used in more than 700,000 clinical uses with no confirmed cases of material rejection. PTFEe is incorporated into surrounding tissue and is minimally encapsulated by collagen. The material is extremely strong and thereby would reduce the need for reoperation for material fatigue. It resists flexural fatigue by acting like a chain when bending forces are applied. However, it is easily cut by a knife or by using die cutting techniques. It lends itself well to machine manufacturing methods including stitching.

Figure 1:
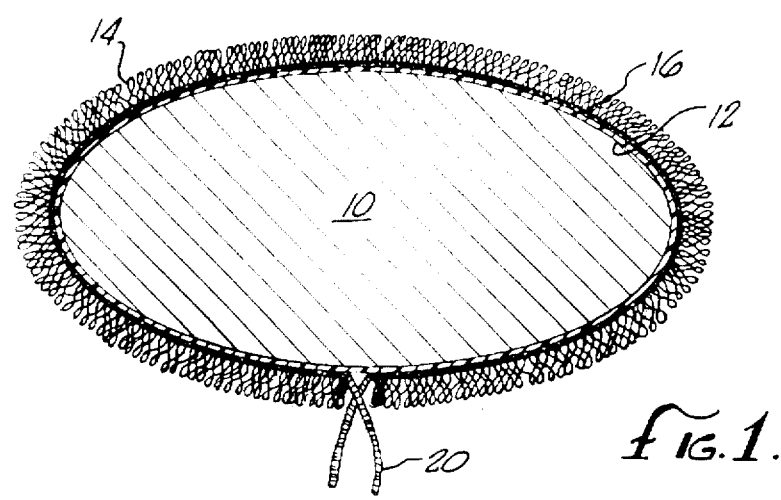
FIG. 1 is a cross-sectional view of a single chambered implant band cover composed of a complex weave of expanded PTFE (PTFEe) filament or ribbon.
Figure 2:
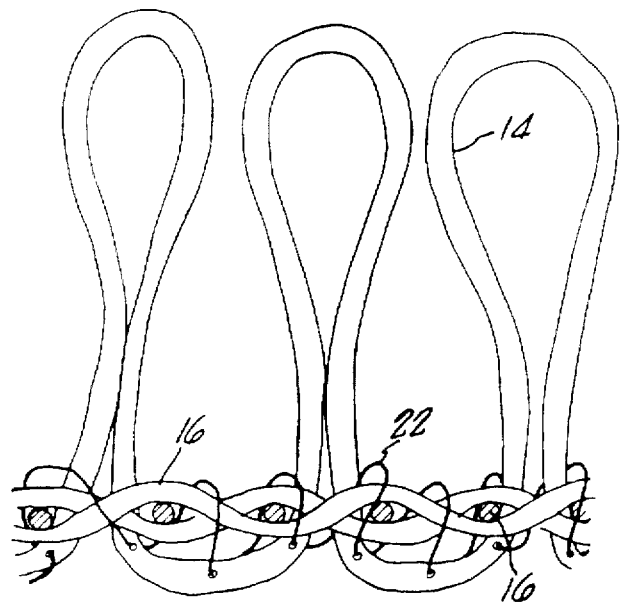
FIG. 2 shows detail of a preferred embodiment of a cover composed of a complex PTFEe filament or ribbon weave affixed to a second stretch material such as Dacron or Nylon which may be impregnated with silicone elastomer.
Figure 8:
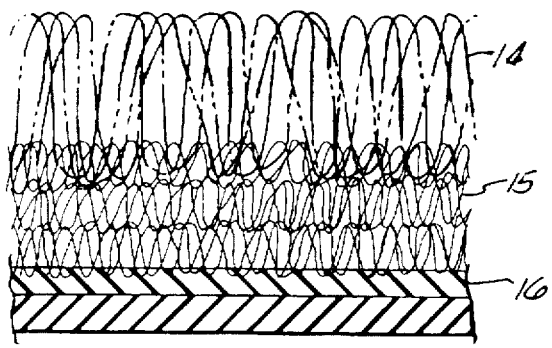
FIG. 8 shows a cross-sectional view of a covering consisting of matted long silicone filaments fused partially to each other and also to a silicone elastomer shell and thereby serving as an anchoring substrate for PTFEe filament or ribbon. The PTFEe may be woven into or sewn or otherwise integrated or affixed to the silicone filaments by sewing or by other suitable means.
Figure 9:
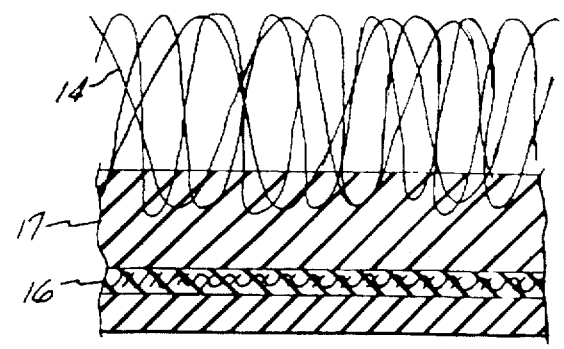
FIG. 9 shows a cross-sectional view of a covering consisting of polyurethane foam, silicone foam or other suitable biocompatible foam serving to provide an anchoring substrate for PTFEe filament or ribbon. PTFEe filament or ribbon may be sewn partially through foam or completely through foam as well as backing consisting of stretch weave material such as Dacron which may be impregnated with silicone elastomer material, or may be otherwise integrated with or affixed to the foam. Materials serving the same functions and possessing characteristics similar to PTFEe may likewise be used.
Figure 10:
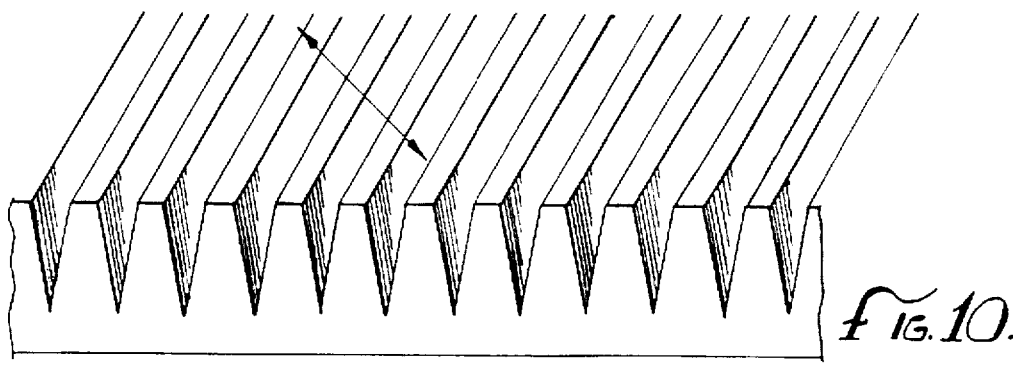
FIG. 10 shows a perspective view of detail of PTFEe sheet material with a partial thickness pattern of simple cuts and/or channels which results in numerous individual villi of PTFEe and great irregularity of the surface of the material. Additional patterns of cuts or troughs may be made along any other axis as indicated, for example, by the arrows.

FIG. 1 shows one embodiment of an implant cover using PTFEe filament or ribbon in a complex expandable weave pattern. The implant 10 has an outer elastomer membrane surface 12 which is covered by the complex PTFEe weave 14. PTFEe filament or ribbon may be woven into a complex stretch weave in the form of a blind sock so as to permit complete envelopment of the implant 10. The weave 14 may be attached to a backing 16, such as a Dacron or Nylon stretch weave embedded in silicone elastomer by sewing or other means. The sock thus formed may be held around the implant 10 by means of a drawstring closure 20 or other suitable means. The sock may be either attached to the exterior surface 12 of the implant, as for example with an adhesive, or may be unattached. If desirable, multiple layers of PTFEe stretch weave socks may be used to envelop the implant 10. FIG. 2 shows detail of fixation of PTFEe filament or ribbon to stretch fabric by sewing through the PTFEe filament or ribbon. The sewing filament 22 is used to affix the weave 14 to the backing 16. As shown in FIG. 8 and FIG. 9, other coverings can be made utilizing silicone elastomer filaments and/or foam as anchoring substrates for PTFEe filament or ribbon. The silicone filaments 15 are matted and may be affixed to backing 16 or left entirely unattached to anything other than PTFEe filament or ribbon 14. Attachment means may be substantially similar to those indicated in FIG. 2. Foam 17 may be affixed to backing 16 by suitable means or may be left entirely unattached to anything other than PTFEe filament or ribbon 14.

Figure 3:
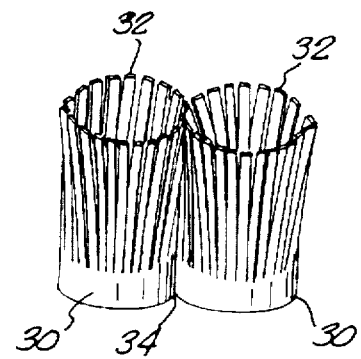
FIG. 3 shows a perspective view of a corona configuration made from a tube of PTFEe which may be sewn into/onto a fabric such as silicone elastomer-impregnated Dacron or Nylon stretch fabric or otherwise affixed or used in other embodiments.

Tubular PTFEe material such as vascular graft material may be cut into a corona configuration as shown in FIG. 3. The corona configuration consists of an unsevered annular region 30 with a plurality of fingers or projections 32 extending from the annular region 30. Two such corona configurations may be formed back to back with the two annular bases 30 being attached in a small region 34. These corona may then be sewn together or to an intermediate backing of stretch Dacron or Nylon fabric or other suitable material in order to form a sock similar to that shown for the complex stretch weave pattern of FIG. 1, or otherwise affixed to the backing or used in other embodiments. Alternatively, the corona structures may be attached directly to the exterior surface or other covering of the implant by other means.

Figure 4:
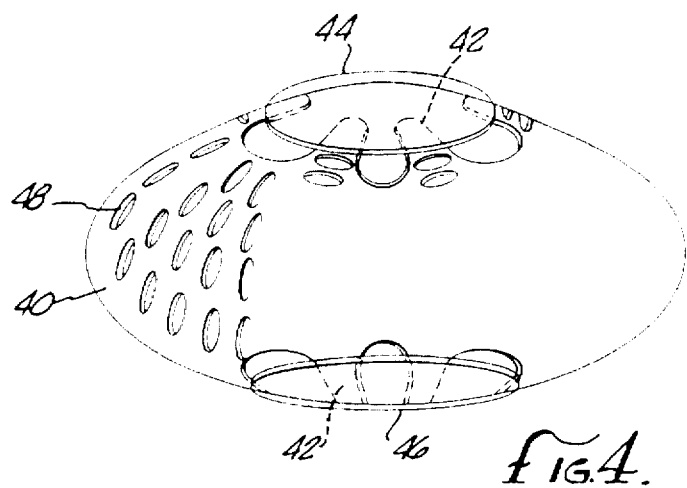
FIG. 4 is a perspective view of an implant covering cut from a single sheet of PTFEe placed around a silicone elastomer shell.

A covering for an implant may be constructed substantially of a single sheet of PTFEe as shown for example in FIG. 4. A single sheet of PTFEe 40 is cut so as to permit it to be wrapped around the implant 10. Projectile tongues 42 may be fastened together or may be attached to separate PTFEe sheets 44 and 46 which serve as cap and bottom pieces. Appropriate cuts 48 are made in the single PTFEe sheet 40 to permit stretching of the sheet in various directions.

Figure 13:
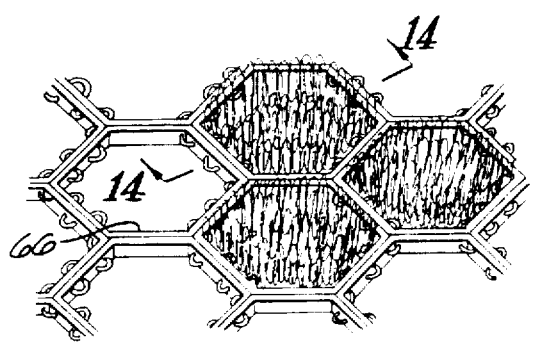
FIG. 13 shows geometric shaped sections of the PTFEe stretch weave affixed to stretch material such as Dacron or Nylon weave, for example, which may be affixed to a molded silicone elastomer shell which is impressed with a hexagonal pattern in relief. A great variety of other geometric patterns as well as PTFEe embodiments may be similarly used.
Figure 14:
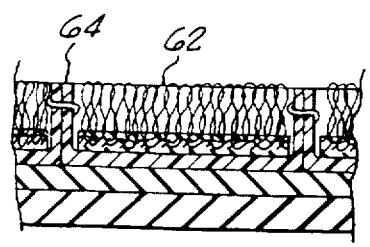
FIG. 14 shows detail of a cover consisting of hexagonal pieces (for example) of PTFEe sheeting sewn to each other or otherwise affixed and used to substantially cover the surface of the implant. The PTFEe may also be used whole (without cuts). Other geometric shapes and embodiments of surface coverings may be similarly used.

It will be appreciated that the PTFEe sheet covering of the implant may be composed of a large number of shapes and sizes of elements. In addition to those embodiments disclosed in detail above, it is possible to use multiple overriding flat sheets sewn to conform to the shape of the implant, overriding or abutting sheets of various geometric shapes as shown in FIG. 13, with stress-relieving patterns of cuts, fan folded or pleated sheets in a cascading pattern to conform to the implant shape, as shown in FIG. 7, or corrugated or pleated sheets as marginal covering over portions of or over the entirety of the implant. Other embodiments include sewing sheets of PTFEe to a backing material made of a stretch material, silicone elastomer sheet or foam material which may be wrapped around the implant or attached to the implant by other suitable means, or by interposing sheets of PTFEe between elements of the implant which may be attached to each other by suitable means as shown in FIGS. 5a, 5b, 6, 25, 26, 27, 28, and 29. Other coverings consistent with the objectives of this invention may be similarly used.

Figure 5A:
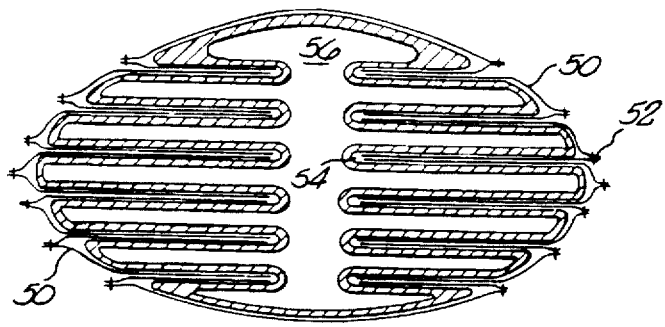
FIGS. 5a and 5b show a cross section of PTFEe sheeting used as a cover for one embodiment of a silicone elastomer shell. Flat sheets with a central cutout are used between disc-like evaginations as well as for coverage of the top and bottom portions of the implant. The pieces are joined to each other by sewing or other suitable means. Two different basic constructions are shown with either a single or multiple sheets of PTFEe used between evaginations.
Figure 5B:
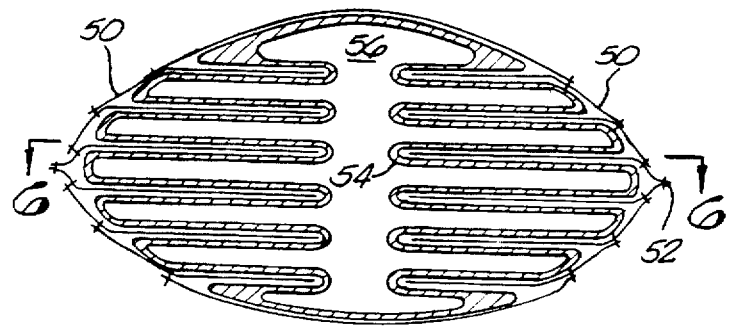
Figure 6:
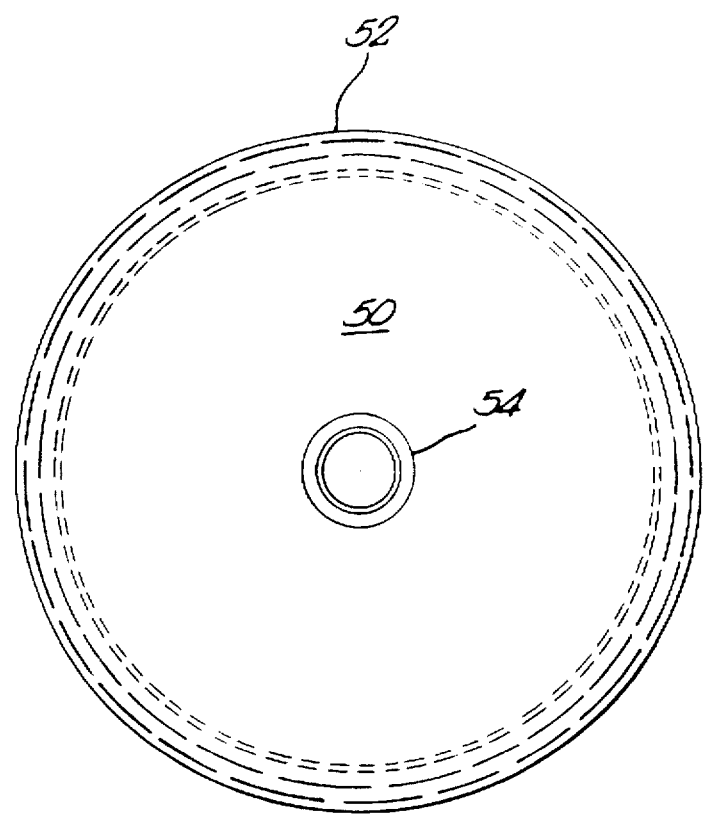
FIG. 6 shows a top view of a PTFEe sheet for covering the implant.
Figure 7:
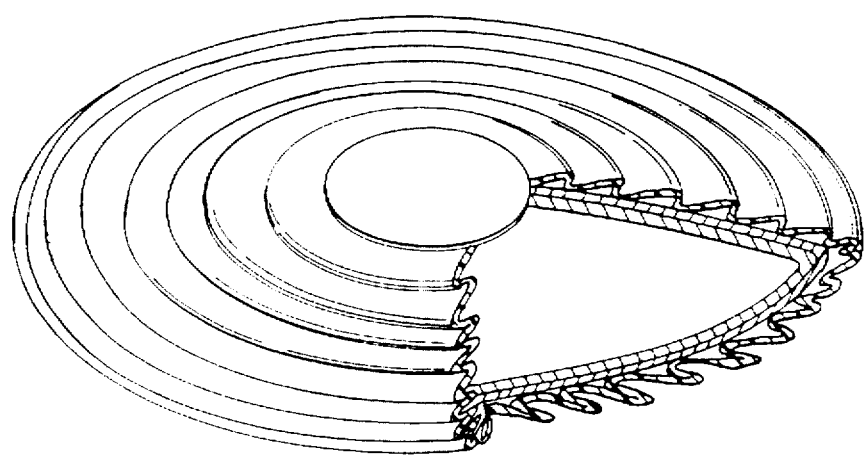
FIG. 7 shows a partial section of another embodiment of PTFEe sheet covering as a cascading series of folds around an implant, with the various sections affixed to a stretch weave material, for example Dacron.

The covering for the implant may be composed of a stack of annular shaped PTFEe sheets as shown, for example, in FIG. 6. Annular sheets of PTFEe 50 may be sewn together or suitably attached at their outer edge 52 and/or at their inner edge 54. When so attached, an interior space 56 defines a plurality of evaginations which are filled by a similarly shaped implant. Two different basic constructions of this covering are shown. FIG. 5a, shows an embodiment with two sheets between evaginations. FIG. 5b, shows an embodiment with one sheet between evaginations.

As in FIGS. 11, 12, 13, and 14, a textured molded covering 58 may be provided made of silicone elastomer or other suitable materials which serves to limit the force of scar contracture around the implant by disorganizing the scar tissue itself and also by compartmentalizing blood clot and collagen around the implant.

Figure 11:
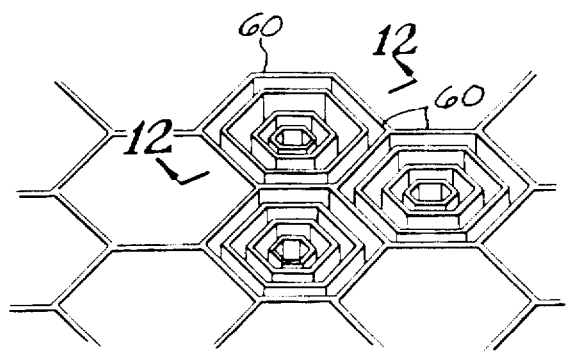
FIG. 11 shows a cover consisting of a molded silicone elastomer shell element with a pattern of nested hexagonal cells over the entire surface of the implant. Detail is shown. Other suitable geometric patterns may also be utilized.
Figure 12:
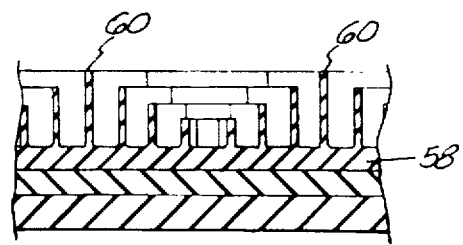
FIG. 12 is a cross-sectional view of the structure of FIG. 11.

The "nested hexcel" structural pattern of FIGS. 11 and 12 is a preferred embodiment. All such hexcels are attached to or part of the same base which is a covering element of the implant. The textured covering 58 may form the entirety or only a portion of the covering of the implant. The hexcel with the largest perimeter 60 in this configuration is also the tallest and delimits hexagonal pools of biologic materials and tissues at the interface between the implant and the body cavity. As scar tissue forms it is forced into concentric, nested rings of scar tissue which do not communicate freely and thus do not contribute to an integral circumferential scar capsule.

It will be appreciated that the height of these nested hexcel structures may be varied. Also the number, diameter or perimeter of the hexcel structures as well as their wall thickness and shapes and characteristics may be varied. It will be further appreciated that a great number of geometric patterns may be utilized for the purposes described above, including square and circular patterns.

It will be appreciated also that the molded textured covering 58 above may be configured to accept a geometric shaped portion of any of the other coverings described herein. A piece of the woven PTFEe stretch weave cover 62, as an example, is sewn or otherwise suitably affixed to the molded covering 58.

Figure 15:
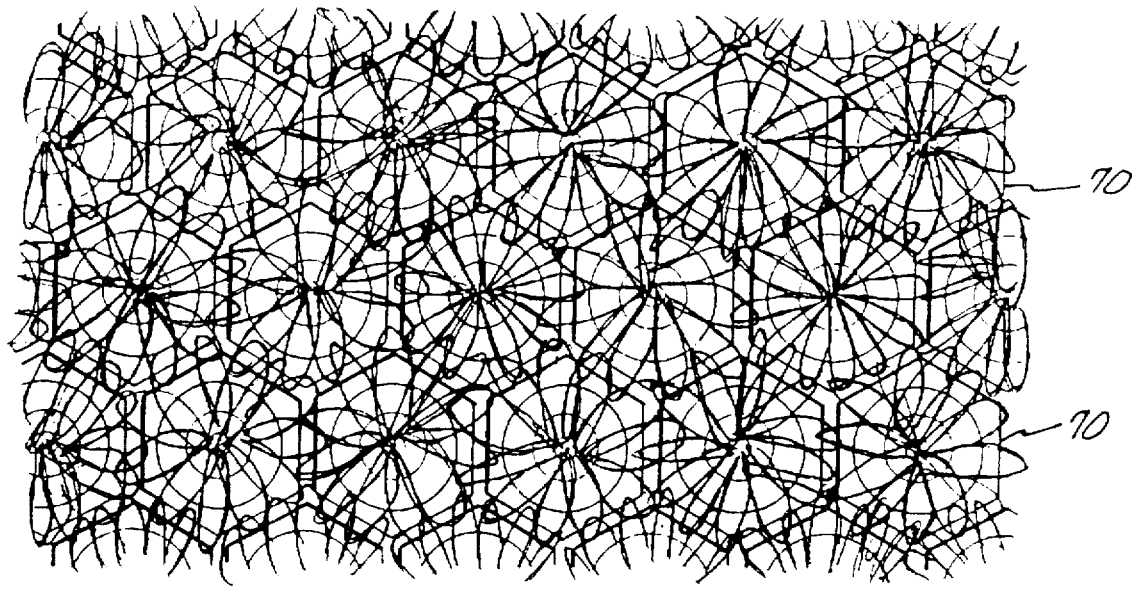
FIG. 15 is a top view of the hexcel arrangement of the cover.
Figure 16:
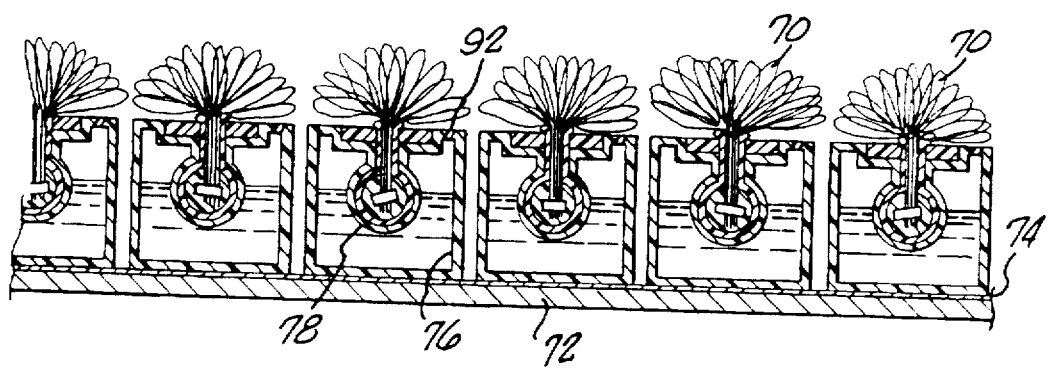
FIG. 16 shows a cross-sectional view of a plurality of hexagonal cells ("hexcels") attached to the surface of an implant. Also shown are bulbous inserts in position in receptacles in the hexcels. Each bulbous insert attaches a spray of PTFEe filament or ribbon to a hexcel.

The covering of the implant may also comprise a plurality of silicone elastomer cells. As shown in FIGS. 15, 16, and 17, in the preferred embodiment, hexagonally shaped cells ("hexcels") 70 may be used. Other configurations would also work well. A plurality of hexcels 70 may be attached to the exterior surface 72 of the implant by silicone adhesive bonding 74 or other suitable means or may be incorporated into a separate covering element such as foam, for example. The hexcels 70 are arranged over the surface 72 of the implant in a mosaic arrangement. The hexcels 70 may be abutting or they may be spaced apart by as far as five millimeters. If necessary, the space between hexcels 70 may be filled with silicone adhesive, foam or other suitable material.

The hexcel 70 is composed of an exterior wall 76 and an internal socket 78. A space 80 is defined between the exterior wall 76 and the internal socket 78. The space 80 may be filled with normal saline or other biocompatible fluid. The space 80 may in addition be filled with foam, or silicone elastomer filaments or other materials which possess the requisite characteristic of offering limited resistance to compression external to the hexcel as well as the characteristics of a great amount of flexibility and deformability. The wall 76 is constructed to offer limited resistance to deformation by varying the wall thickness. An insert 80 is placed in socket 78. As shown in detail in FIG. 17, the insert 82 is composed of an enlarged section 84, strands of PTFEe filament or ribbon 86, a clip 88 and a surface piece 90. The enlarged section 84 is received by the socket 78 and held in place thereby. In this embodiment a slight amount of rotational and flexural movement on the part of the insert 82 is permitted. The clip 88 is preferably a radiolucent plastic vascular clip crimped to hold the PTFEe filaments or ribbons 86 within the enlarged molded section 84. The surface disc 90 is made of solid PTFE or PTFEe sheeting or other suitable material and may be used to stabilize the hexcel structure. It will be appreciated that the PTFEe material may be in any number of forms, for example, in the filament or ribbon form as shown herein, or in any other format provided that it can be retained by the hexcel.

Relief holes 92 may be provided in the hexcel 70 to make the hexcel more compressible. In the event of capsular contracture the outer surfaces of the hexcel 70 will be compressed towards the implant surface 72 thereby increasing the pressure of materials contained within the space 80. If the pressure within the space 80 exceeds the pressure outside the relief hole 92, biocompatible fluid such as normal saline will be injected into the body at a rate equal to the contracture rate, thereby decreasing the overall volume of the implant slightly and yet retaining implant suppleness, softness and shape.

An interior compressive structure may be provided within the implant as shown in FIG. 18. The implant may contain multiple enveloping membranes 94 as well as multiple enveloping compartments 96, any number of which may contain gel or normal saline or other biocompatible fluid, foam or other suitable material. An internal compressive structure 100 may be provided which is made of silicone elastomer and which may be configured to incorporate a plurality of evaginations 102, which compressive structure 100 contains a gas in the innermost chamber 98. A special coating consisting of a polysiloxane or other appropriate material may be applied to prevent gas diffusion through the wall of the evaginated structure 102. Normal saline, gel or other suitable material is used in spaces 96 to transmit pressure between fluid or gel-filled compartments 96, and elastomer evaginations 102. The fluid passes through the perforations 106. The various enveloping membranes 94 may be affixed to each other in a region, for example 104, if desired.

Another preferred embodiment is that of utilizing a plurality of the compressive structures shown in FIG. 18 inside a gel-filled or normal saline-filled implant along with a larger compartment of gel or normal saline or other-configured portion of an implant.

Multiple enveloping compartments may be provided that can be serially decompressed. Radiopaque and independently targetable regions of such compartments may be provided in order to permit the outermost compartment then still containing fluid to be selected for decompression by insertion of a hollow needle or other suitable device. Alternatively, pressure sensitive valves may be provided to permit spontaneous decompression without surgical intervention.

Figure 22:
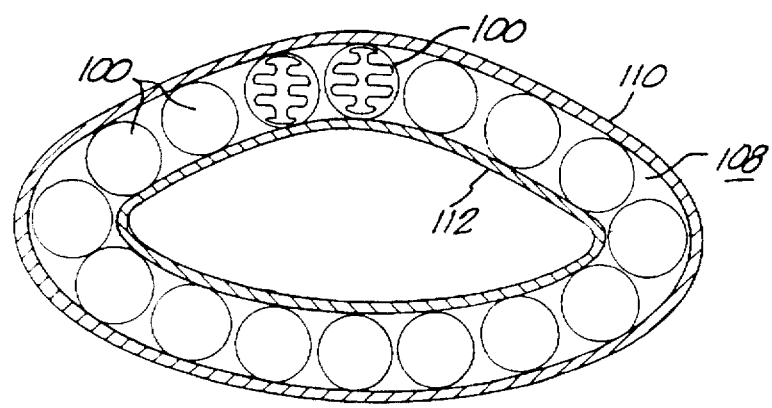
FIG. 22 is a cross-sectional view of an implant which shows a plurality of the pressure accommodation elements described in FIG. 18 inside a gel or saline-filled chamber which is itself located outside a larger compartment of gel or normal, saline or other-configured portion of an implant. These pressure accommodation elements may be affixed to the outer and/or inner elastomer shell(s) or may be permitted to float freely within the saline or gel matrix.
Figure 24:
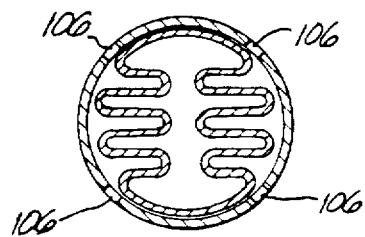
FIG. 24 is an enlarged view of the cross-section of the compressible member of FIG. 23.

A plurality of pressure accommodation elements 100 may be provided as described in FIG. 22. These elements are situated in a compartment 108 which is also filled with silicone gel or normal saline or other suitable fluid and the compartment 108 may be located outside of or surrounding a separate compartment of gel or normal saline or other portion of an implant. These pressure accommodation elements may be affixed to the outermost elastomer shell 110 or to the inner elastomer membrane 112 or both or may be permitted to float freely within the fluid or gel inside the compartment 108. FIG. 24 shows detail of the compression structure 100. One or more vent holes 106 may be employed for equilibration of pressures.

Figure 23:
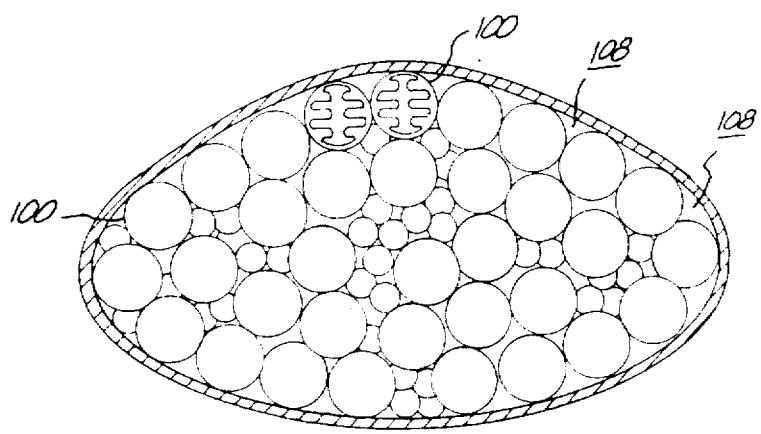
FIG. 23 is a cross-sectional view of an implant containing a plurality of gas and/ or fluid containing compressible members within the implant which also contains fluid or gel. Each typical pressure-accommodation element is a small version of the element described in FIG. 18.

As described in FIG. 23, another preferred embodiment is that of an implant containing a plurality of gas and/or fluid and/or foam containing compressible members within the implant which also contains fluid or gel. Each typical pressure-accommodating element may be a small version of the element described in FIG. 18.

Figure 20:
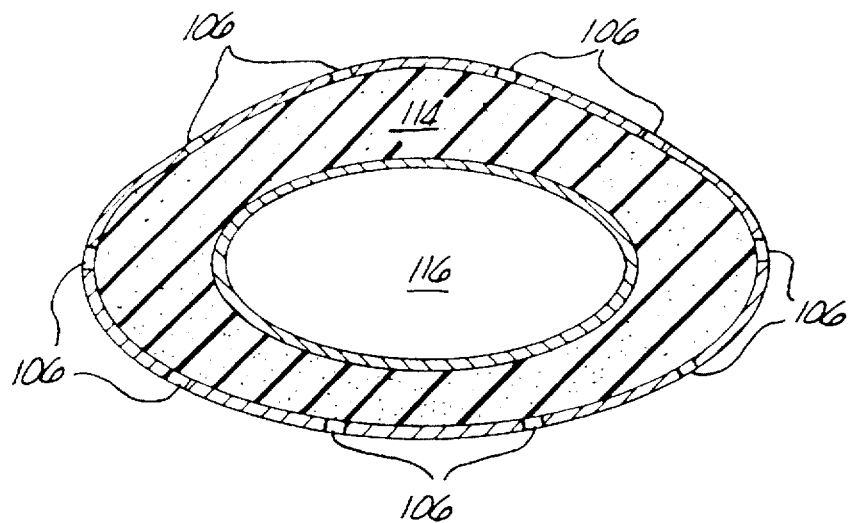
FIGS. 20 and 21 show cross-sectional views of a pressure accommodation element consisting of a polyurethane or other biocompatible foam cover enveloping substantially all or part of a gel-filled or other-configured implant. The foam is itself covered with a perforated silicone elastomer or PTFEe membrane or other suitable material. The cover is perforated or has other fluid conducting structures which permit ingress and egress of normal saline or body fluids. The foam is filled with normal saline or other biocompatible fluid at implantation of the prosthesis.
Figure 21:
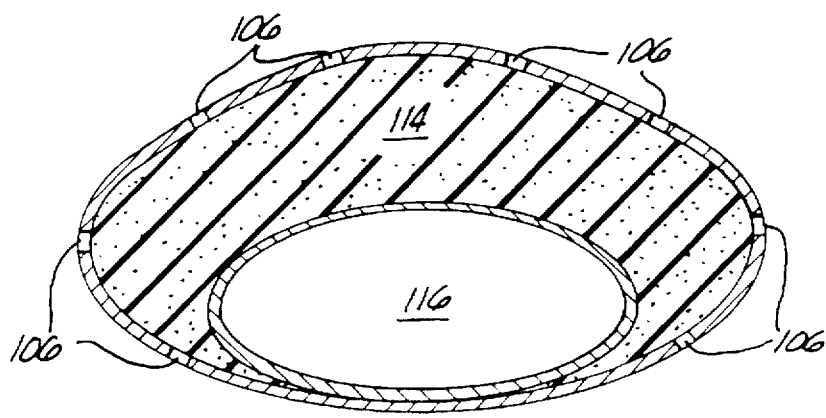

Other compressive structures as shown in FIGS. 19, 20 and 21 may be provided which incorporate polyurethane or other biocompatible foam 114 filled with normal saline and which may be placed substantially around or within another separate compartment 116 filled with silicone gel or normal saline or other biocompatible fluid. Each such fluid-filled foam element accommodates to compression external to the implant by bleeding off biocompatible fluid sufficient to equal such compression via a number of perforations or tubes between the foam-filled space and the space surrounding the implant. The foam-filled space may in addition contain semi-compressive sac-like structures or a trabecular network of silicone elastomer walls or filaments which may provide additional resistance to compression of the foam and thereby limit the collapse of the space in compartment 116. The fluid that is drained off is absorbed by the body. It will be appreciated that there may be a plurality of such small fluid-filled foam elements comprising yet another configuration of this embodiment. FIG. 21 shows the compartment 116 attached to the outer cover of the implant, as an example.

Figure 25:
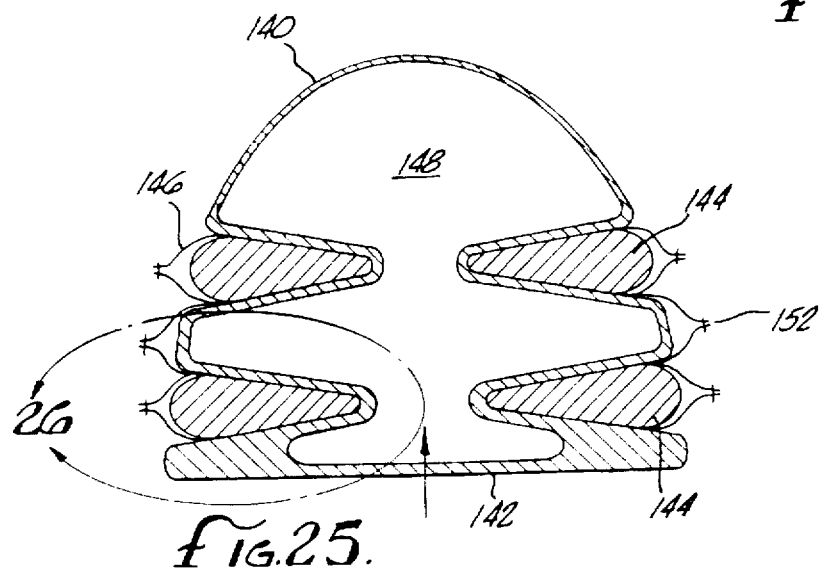
FIG. 25 shows a cross-section of a telescoping projection element which may be configured as the mammary prosthesis proper or may be configured as a projection element of a more complex implant. Toroid elements may be solid or fluid-filled and serve to restrict horizontal displacement of the shell, yet permit vertical expansion. The apical portion of the expansion chamber is made thin in order to permit preferential dilatation of this region.
Figure 26:
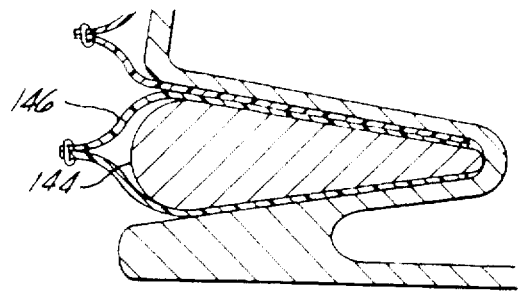
Figure 27:
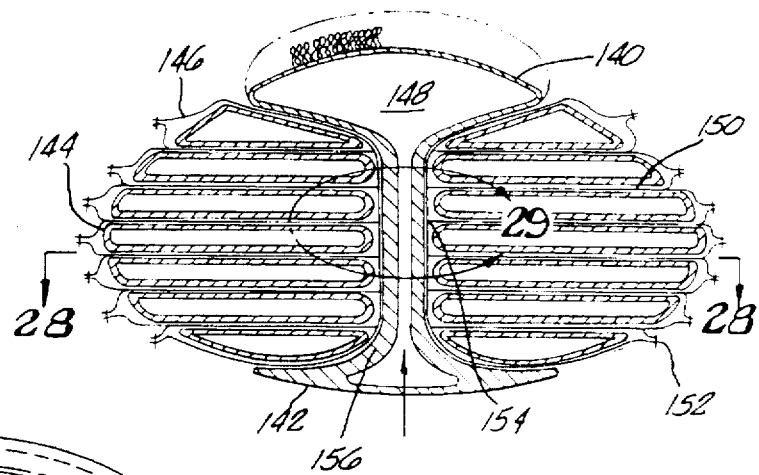
FIG. 27 shows a cross-section of an implant consisting of a stack of either hollow or solid toroid elements held in apposition by a projection element that traverses the central opening of each toroid element and which by virtue of the enlarged top and bottom portions serves to maintain all elements of the implant in intimate contact. The apical portion of the projection element is an expansion chamber which may be filled through the bottom or top piece. The surfaces of the toroid elements are protected by a covering of PTFEe sheets which are sewn or otherwise affixed to each other at the greater periphery. The tube is shown covered by tubular PTFEe to minimize friction.
Figure 30:
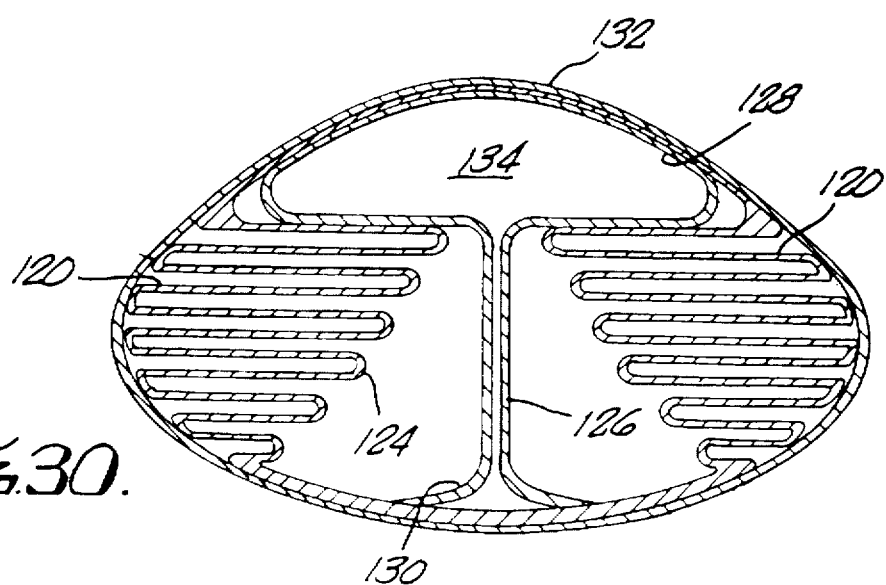
FIG. 30 shows a cross-sectional view of a silicone elastomer implant consisting of a series of hollow or solid discoid evaginations of different diameters whose overall configuration is that of a standard mammary prosthesis. Also shown is a special internal projection element at the apex with a stalk affixed to the base of the implant. Also shown is an outermost silicone elastomer membrane which serves to provide for smooth contouring of the implant.

The use of a plurality of fluid-filled or gas-filled or solid discoid elements, connected to each other at the central constriction (narrow waist), such as shown and described in connection with FIGS. 5a, 5b, and 30, and expandable discoid evaginations as shown and described in connection with FIGS. 25 and 27, are preferred embodiments. These discoid elements may have varying sizes and shapes. The diameter of each disc or evagination may be set as needed. In one preferred embodiment as shown for example in FIG. 30, a relatively large distance will separate the inside portions 124 of the evaginations 120 closest to the chest wall. This space will decrease as the opposite pole of the implant is approached. In this way, greater stability and axial projection of the implant may be achieved. Additional stabilization may be achieved by changing the shape of the central tube 126. Attachment of the projection element 128 is by means of a flared portion 130 of the tube 126 or by other suitable means. If desired, an expandable region may be included which comprises a relatively more distensible and thin walled section of the exterior surface 132 of the implant as well as a chamber 134 in which normal saline or other biocompatible fluid may be used to provide pressure to expand the thin walled region of the exterior membrane 132 of the implant. It will be appreciated that the implant may be covered with any of the coverings described herein.

Figure 28:
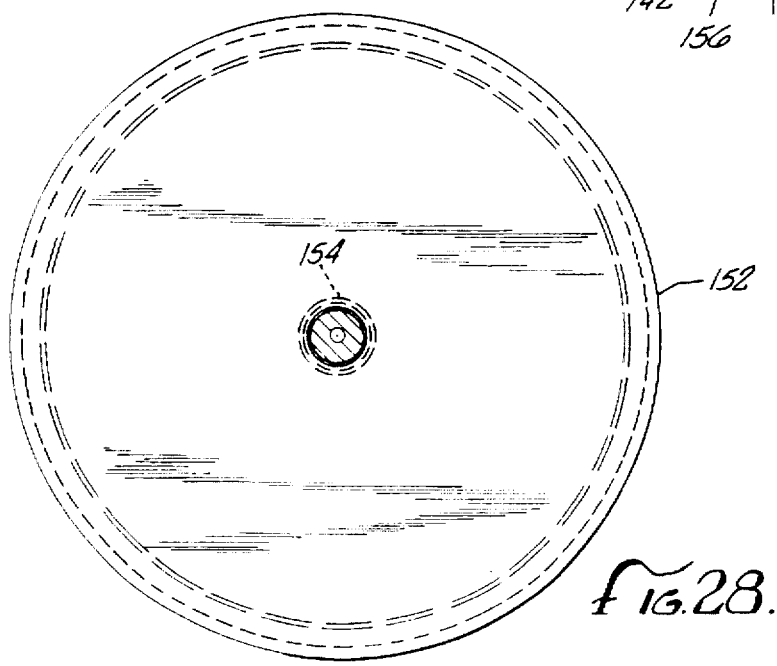
FIG. 28 is a plan view of the structure shown in FIG. 27.
Figure 29:
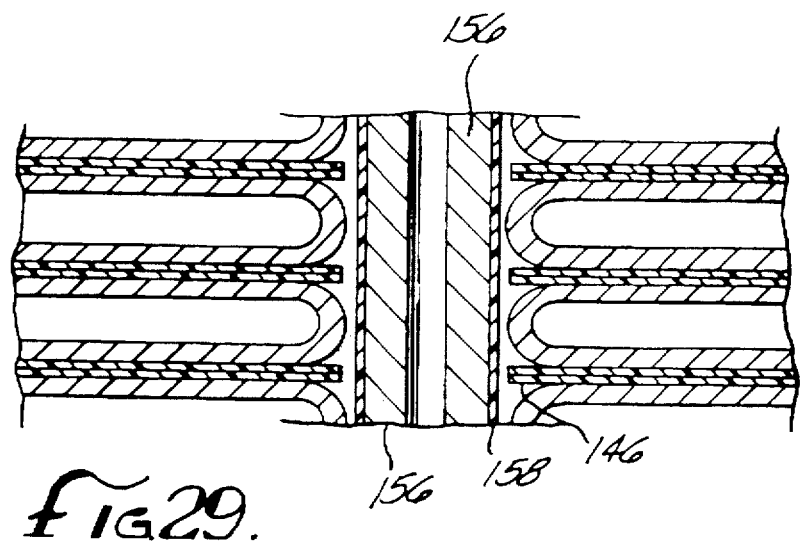
FIG. 29 is an enlarged detail of FIG. 27.

FIGS. 27, 28, and 29 show the use of a plurality of fluid-filled or solid toroid-shaped elements, maintained in apposition by a projection element with a tubal element 156 that traverses the central opening of each element. This is a preferred embodiment of the invention. The enlarged top 140 and bottom 142 portions serve to maintain all elements of the implant in intimate contact. Either the top or bottom portion or other portions of the projection element may serve as an expansion chamber 148 which may be filled through either the bottom or top piece or both. The surfaces of the toroid elements 144 are protected by a covering of PTFEe sheeting 146 which serves to reduce friction at the interfaces 150 as the implant is manipulated. The PTFEe sheets are affixed to each other by suitable means at the greater periphery 152, the lesser periphery 154, or both. Likewise the tubal element 156 is covered by tubular PTFEe 158 to reduce friction. It will be appreciated that the individual sub-elements of this embodiment may be configured in a great variety of ways. It will also be appreciated that any portion of or the entirety of the implant may be covered by any of the coverings described herein.

Though the invention has been described with respect to specific preferred embodiments, many variations and modifications will become apparent to those skilled in the art. It is therefore the intention and expectation that the appended claims be interpreted as broadly as possible in view of the prior art in order to include all such variations and modifications.

What is claimed is:

1. A covering for an implantable prosthetic device for use in the human body comprising:

at least one pressure sensitive structure, said at least one pressure sensitive structure enclosing a volume for containing a fluid, a gas or a combination of both, and a means for communication between the volume of said pressure sensitive structure and the human body, and an atraumatic covering for at least that portion of the pressure sensitive structure adapted to interface with the human body.

* * * * *